United States Patent [19]

Schmidt et al.

[11] Patent Number: 5,068,182
[45] Date of Patent: Nov. 26, 1991

[54] SUBSTRATES AND REAGENTS USEFUL IN DETERMINING α-AMYLASE AND A METHOD FOR DETERMINING α-AMYLASE

[75] Inventors: Axel Schmidt, Munich; Herbert Von Der Eltz, Weilheim; Elli Rauscher, Munich, all of Fed. Rep. of Germany

[73] Assignee: Boehringer Mannheim GmbH, Mannheim, Fed. Rep. of Germany

[21] Appl. No.: 288,471

[22] Filed: Dec. 22, 1988

[30] Foreign Application Priority Data

Dec. 23, 1987 [DE] Fed. Rep. of Germany ....... 3743908

[51] Int. Cl.$^5$ .......................... C12Q 1/40; C07H 5/04
[52] U.S. Cl. ......................... 435/22; 435/14; 536/18.7; 536/115; 536/118; 536/119
[58] Field of Search ................. 536/6.5, 7.4, 18.7, 536/115, 118; 435/14, 22

[56] References Cited

U.S. PATENT DOCUMENTS

| | | |
|---|---|---|
| 4,102,747 | 7/1978 | Driscoll et al. |
| 4,145,527 | 3/1979 | Burns et al. |
| 4,147,860 | 4/1979 | Farnham et al. |
| 4,233,403 | 11/1980 | Menson et al. |
| 4,451,563 | 5/1984 | Kaufman |
| 4,521,592 | 6/1985 | Dahmen et al. |
| 4,544,631 | 10/1985 | Rauscher et al. |
| 4,550,077 | 10/1985 | Woodbridge et al. |
| 4,563,421 | 1/1986 | Habenstein et al. |
| 4,622,295 | 11/1986 | Ikenaka et al. |
| 4,649,108 | 3/1987 | Blair |
| 4,697,006 | 9/1987 | Ikenaka et al. |
| 4,709,020 | 11/1987 | Rauscher et al. |

FOREIGN PATENT DOCUMENTS 60087297 10/1983 Japan .
60237998 12/1983 Japan .

OTHER PUBLICATIONS

Kochetkov et al.—Chem. Abst. vol. 68 (1968) p. 22173q.
Cheetham et al.—Chem. Abst. vol. 104 (1986) p. 22173q.
Klein et al.—Chem. Abst. vol. 104 (1986) p. 168,764s.
Laesceke, et al., Liebigs Ann. Chem. 1983: 1910–1919 (1983).
Omichi, et al., J. Biochem. 93: 1055–1060 (1983).
Matsui, et al. *Japan Clinical Chemistry Association Summer Seminar* Jul. 1982, pp. 199–202.
Marshall, Anal. Biochem. 85: 541–549 (1978).
Marshall, et al. Clin. Chem. Acta. 76: 277–283 (1977).
"Biomedix Brochure" (Becton-Dickinson, 1980).

*Primary Examiner*—Sam Rosen
*Attorney, Agent, or Firm*—Felfe & Lynch

[57] ABSTRACT

The present invention provides compounds of the general formula

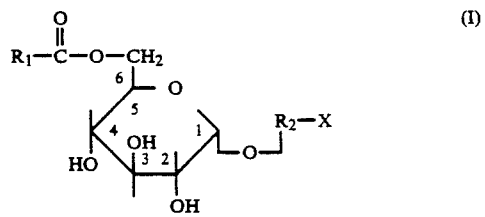

wherein $R_1$ is a hydrogen atom, a methyl, ethyl, propyl, isopropyl, butyl, tert. butyl or 1-alkoxyalkyl radical or an optionally hydrophilically substituted cyclopropyl, cyclobutyl, cyclopentyl, cyclohexyl, phenyl, tetrahydropyranyl, piperidinyl, N-methyl substituted piperidinyl or N-ethyl substituted piperidinyl, pyridinyl, thiophenyl or 1,1-dioxo-tetra- hydrothiopyranyl radical or an amino group which is optionally substituted by the same or different substituents selected from methyl, ethyl, propyl and isopropyl radicals. $R_2$ is an oligoglucoside residue with 2, 3 or 4 glucose units and X is a hydrogen atom or an optically determinable residue. The present invention also provides processes for the preparation of compounds (I) and reagents for the determination of α-amylase containing them. Furthermore, the present invention provides a process for the determination of α-amylase using a compound of general formula (I).

12 Claims, No Drawings

SUBSTRATES AND REAGENTS USEFUL IN DETERMINING α-AMYLASE AND A METHOD FOR DETERMINING α-AMYLASE

The present invention is concerned with new oligoglucoside derivatives, processes for the preparation thereof and the use thereof as substrates for the determination of α-amylase.

The determination of α-amylase in serum and urine is an important clinical parameter for the examination of the function of the pancreas. In the case of the most common processes for the determination of α-amylase, as substrates oligoglucosides which consist of 3 to 8 1,4-α-linked glucose units and are derivatized in the 1-position on the reducing end with a determinable group and on the other end, in the 6- and possibly 4- position, with a protective group are used as substrates.

U.S. Pat. No. 4,709,020 describes such substrates which are derivatized with a determinable radical, for example a nitrophenyl radical, in the 1-position on the reducing end and with a protective group in the 4- and 6-position on the other end. Straight-chained or branched alkyl and alkoyl radicals, phenyl radicals and ethylidene bridges are examples of usable protective groups.

The carrying out of an α-amylase determination test with such substrates as enzymatic color tests has been described for the substrate 4,6-ethylidene-p-nitrophenyl-α-D-maltoheptaoside (Et-G7-PNP) by Fresenius (see Z. Anal. Chem., 324, 304–305/1986) The determination takes place according to the following simplified test principle:

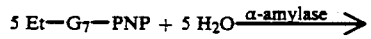

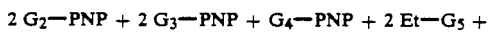

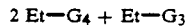

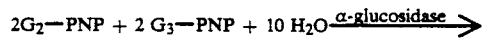

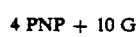

(Et = ethylidene, G = glucose, PNP = p-nitrophenyl).

The advantage of these substrates lies especially in the fact that the auxiliary enzymes which are used for the liberation of the determinable residue, for example α-glucosidase or β-glucosidase, only attack the substrate already cleaved by α-amylase but not the non-cleaved substrate. In this way, better storage stability of the reagent mixture in comparison with the unprotected substrates is achieved.

However, for increasing the precision, especially in the case of the determination of small α-anylase activities, it is desirable to have α-anylase substrates with still higher sensitivity in photometric tests that can be achieved with the known substrates. By sensitivity as used herein, it is understood to refer to the ratio of α-anylase activity to the extinction increase per unit time (ΔE/min). Thus, an increase of the sensitivity means that, using the same α-amylase activity of the sample, a greater ΔE/min is found.

Therefore, it is an object of the present invention to provide α-amylase substrates which are storage-stable and display improved sensitivity.

Thus, according to the present invention, there are provided compounds of the general formula:

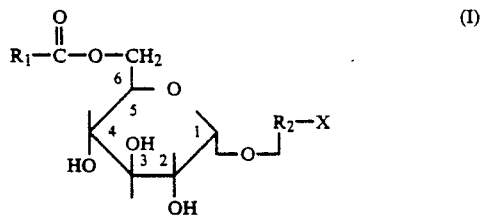

wherein $R_1$ is a hydrogen atom, a methyl, ethyl, propyl, isopropyl, butyl, tert, butyl or 1-alkoxyalkyl radical or an optionally hydrophilically substituted cyclopropyl, cyclobutyl, cyclopentyl, cyclohexyl, phenyl, tetrahydropyranyl, an optionally N-methyl- or ethylsubstituted piperidinyl, pyridinyl, thiophenyl or 1,1-dioxotetrahydrothiopyranyl radical or an amino group which is optionally substituted by the same or different substituents selected from methyl, ethyl, propyl and isopropyl radicals, $R_2$ is an oligoglucoside residue with 2, 3 or 4 glucose units and X is a hydrogen atom or an optically determinable residue.

Surprisingly, we have found that the substrates according to the present invention with the above-mentioned protective groups in the C6-position are distinctly more sensitive than the known substrates and the precision of the α-amylase determination can be substantially improved therewith.

$R_1$ is preferably a methyl, isopropyl or optionally hydrophilically substituted cyclopropyl radical. The isopropyl and cyclopropyl radicals are especially preferred $R_2$ is preferably a hydrogen atom. $R_2$ is preferably an oligoglucoside residue with 4 glucose units.

The hydrophilic substituents can be, for example, carboxyl, hydroxyl, sulphonic acid, dimethylamino, phosphate, halogen and/or nitro groups The optically determinable residue in the 1-position on the reducing end of the substrate can be attached not only in α-configuration but also in β-configuration.

If X is an optically determinable residue, it can be a radical which itself displays a color in the visible or UV range or it can be a residue which can be determined optically only after reaction with a further compound, for example by conversion into a colored material or by coupling with a colored material Such optically determinable residues are well known to the expert and do not require any detailed explanation here. Nitro group-containing and optionally chlorinated phenyl radicals are preferred, such as a nitrophenyl, 3,4-dinitrophenyl or 2-chloro-4-nitrophenyl radical, as well as resorufin and derivatives thereof. In case of 4- and 6-bridged substrates X is preferably chlorinated nitrophenyl- or a resorufin.

The preparation of the compounds according to the present invention and of the comparative compounds takes place analogously to the process described in U.S. Pat. No. 4,709,020. The desired protective group can also be introduced into the unprotected substrate via activated carboxylic acid groups, for example via the corresponding ortho esters, acid chlorides, anhydrides, from activated esters enzymatically (J.A.C.S., 110, 584–589/1988), via acetals or directly via carboxylic acids and water-removing agents, for example by means of the Mitsunobu reaction, (Czernecki, Synthesis 1981, pp. 1–28). Especially preferred is the preparation via the corresponding ortho esters as intermediate products and via the Mitsunobu reaction. The ortho esters are preferably prepared from the corresponding nitriles (cf. for example Houben-Weyl, Vol. V$_I$/3. 300–313/1965). The nitriles can be prepared, for example, from the corresponding carboxylic acids. The protected substrates can be purified, for example, by chromatography such as ion exchange chromatography or MPLC.

The present invention also provides a process for the preparation of the compounds of general formula (I), wherein compounds of the general formula

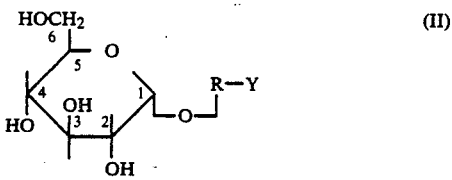

wherein R is an oligoglucoside residue with 2, 3 or 4 glucose units and Y is a hydrogen atom or an optically determinable residue, are reacted in known manner with carboxylic acids, optionally additionally activated esters thereof, orthoesters, acetals or ketals of the general formula:

wherein $R_4$ is a hydrogen atom, a methyl, ethyl, propyl, isopropyl, butyl, tert. butyl or 1-alkoxyalkyl radical or an optionally hydrophilically substituted cyclopropyl, cyclobutyl, cyclopentyl, cyclohexyl, phenyl, tetrahydropyranyl, an optionally N-methyl- or ethyl-substituted piperidinyl, pyridinyl, thiophenyl or 1,1-dioxotetrahydrothiopyranyl radical or an amino group which is optionally substituted by the same or different substituents selected from methyl, ethyl, propyl and isopropyl radicals, $R_5$ is a hydrogen atom, a hydroxy, alkyl or alkoxy radical or a dimethyl- or diethyl-substituted amino group and $R_6$ and $R_7$ which can be the same or different, are methoxy or ethoxy radicals or represent a single oxygen atom, in the presence of an acid catalyst or water-removing agents in an anhydrous solvent with the exclusion of moisture. Subsequently, the product mixture is optionally hydrolyzed and, for example, chromatographically purified. Preferably, the reaction temperature is between 20° and 50° C.

According to this procedure compounds of the general formula (I), wherein $R_1$ is a methyl, isopropyl or an optionally hydrophilically substituted cyclopropyl radical, $R_2$ is an oligoglucoside with 4 glucose units and X is a resorufin or p-nitrophenyl, are obtained when compounds of the general formula (II), wherein R and Y have the above-given meanings for $R_2$ and X, and at least 4 times of the molar amount of an orthoester of the generaly formula (III) wherein $R_3$ is a methyl or isopropyl radical, $R_4$ is a methoxy or ethoxy radical and $R_5$ and $R_6$ each a methoxy or ethyoxy radical are dissolved in a anhydrous solvent with 1 mol p-toluenesulphonic acid, with the exclusion of moisture, 4,6-ethylidene-resorufinyl-,β-D-maltopentaoside or 4,6-ethylidene-p-nitrophenyl-α-D-maltopentaoside were analogously produced from acetals of the general formula (III), wherein $R_3$ is a methyl radical, $R_4$ is a hydrogen atom and $R_5$ and $R_6$ each are a methoxy radical, and compounds of the general formula (II). Instead of p-toluenesulphonic acid other organic acids as well as mineral acids and/or Lewis acids have proved to be useful as catalysts.

The preparation of the compounds according to the invention from carboxylic acids of the general formula (III), wherein, for example, $R_3$ is a methyl, isopropyl or hydrophically substituted cyclopropyl radical, $R_4$ is a hydroxy or a carboxylic acid-activating radical and $R_5$ and $R_6$ are together an oxygen atom and compounds of the general formula (II) is also preferred. This reaction takes place in the presence of one or more water-removing agents with the exclusion of moisture.

Water-removing agents are, for example, triphenylphosphine and/or diethylazodicarboxylate and/or other compounds which are usable in this way.

By alkoxyalkyl in the definition of $R_1$ and $R_3$ is to be understood alkoxy linked to alkyl wherein each of them contains 1 to 6, preferably 1 to 4 carbon atoms. Alkyl in the definition of $R_4$ contains 1 to 6 preferably 1 to 3 carbon atoms.

Alkoxy in the definition of $R_4$ contains 1 to 10, preferably 1 to 6 carbon atoms and optionally one or more hetero atoms, preferably nitrogen or chlorine, and can be straight-chained, branched or cyclic.

The preparation of the compounds can also take place by peracetylation of the particular glucoside (maltotrioside, maltotetraoside, maltopentaoside) with acetic anhydride or acetyl chloride (Chem. Ber., 13, 267/1880) and by hydrolysis of the 1-positoned acetoxy radical (Chem. Ber., 86, 604/1953) to the hydroxide or bromide. Subsequently, the free colored material is coupled on to the glucoside by means of the chloroacetimidate method (Synthesis, 1981, 885–887) or the Königs-Knorr method (J.A.C.S., 51, 1980/9129; Angew. Chem., 94, 184/1982).

The coupling can also take place directly by reaction of the particular peracetylized glucoside with a phenolic chromogen and a Lewis acid as a catalyst (JP 62/289595). After coupling of the colored material, deacetylation is carried out and the protective group is coupled on to the terminal 4- and/or 6-position via the corresponding ortho esters, acetals, enzymatically or via the activated carboxylic acid derivatives, such as active esters, acid chlorides or anhydrides (Tetrahedron Letters, 28, 3809–3812/1987; J.A.C.S., 108, 5638/1986). The compounds used for comparison experiments are prepared analogously.

The present invention also provides a process for the determination of α-amylase in a sample by reaction with an oligosaccharide substrate, α-9lucosidase and/or β-glucosidase and determination of the cleavage products, wherein, as oligoglucoside substrate, there is used a compound according to the present invention of general formula (I).

Insofar as X is a hydrogen atom, the determination of the cleavage products can take place in a manner known to the expert, for example as described in U.S. Pat. No. 4,544,631. The determination of the cleavage products when X is an optically determinable residue is also known to the expert and is described, for example, in U.S. Pat. No. 4,709,020. In a further embodiment, glucoamylase is additionally added thereto.

The present invention also provides a reagent for the determination of α-amylase comprising (end concentrations in the test):

0.5–2 mMole/liter of substrate according to the present invention 30–100 mMole/liter sodium chloride 20–50 U/liter α-glucosidase and/or 0.5–2 U/ml β-glucosidase.

The determination is usually carried out in a buffer, preferably in GOOD buffer with a pH of 6 to 8, preferably of 6.5 to 7.5 and a concentration of 20 to 200 mMole/liter, preferably of 50 to 150 mMole/liter. 5–20 U/ml glucoamylase can optionally be added thereto. The determination is preferably carried out in the presence of 5 to 20 mMole/liter magnesium chloride.

The following Examples are given for the purpose of illustrating the present invention:

EXAMPLE 1

Peracetyl-β-D-malgopentaoside 100 g (0.12 mole) maltopentaose and 81.8g (1.0 mole) anhydrous sodium acetate are suspended in 1.1 liters (11.7 mole) acetic anhydride and slowly heated, with the exclusion of moisture, until commencement of the reaction (about 110° C.). The reaction mixture is then cooled with ice water until the reaction has subsided and subsequently boiled under reflux for 1 hour for completion of the reaction. The reaction mixture is cooled to about 70° C. and poured into 4 liters of ice water. After stirring for 60 minutes, the supernatant is poured off and the residue dissolved in 500 ml dichloromethane. The dichloromethane phase is successively shaken out with water, a saturated aqueous solution of sodium hydrogen carbonate and water and then dried over anhydrous sodium sulphate. After distilling off the solvent in a vacuum, the residue is recrystallized from 1.5 liters of ethanol-isopropanol (1:1 v/v), with the addition of active charcoal. Yield: 166.2 g (89.8% of theory) of colorless crystals; m.p. 120°–125° C.; $\alpha_D^{20}$ = +123.5° TLC: silica gel 60 plates $F_{254}$ (Merck): toluene/acetone (7:4 v/v) Rf =0.52.

$^1$H-NMR (DMSO-d$_6$): 1.8–2.2 (s, 51H, CH$_3$CO); 3.8–5.5 (m, 35H, H-1–H-6).

Literature Herzfeld, Chem. Ber., 13: 267/1880.

The following peracetyl-β-D-maltooligosaccharides were synthesized in the above-described manner: instead of maltopentaose, the same amounts of maltose, maltotriose, maltotetraose, maltohexaose and maltoheptaose were used.

| sugar | m.p. | yield | $\alpha_D^{20}$ (CHCl$_3$) | Rf (silica gel 60; toluene: acetone = 7:4 v/v) |
|---|---|---|---|---|
| maltose | 159–160° C. | 90% | +62.5° | 0.64 |
| maltotriose | — | 85% | +100.3° | 0.59 |
| maltotetraose | — | 88% | +109.7° | 0.56 |
| maltopentaose | 120–125° C. | 90% | +123.5° | 0.52 |
| maltohexaose | 140–145° C. | 91% | +130° | 0.49 |
| maltoheptaose | 160° C. | 82% | — | 0.46 |

EXAMPLE 2

Hydroxy-α-D-peracetylmaltopentaoside 150 g. (0.096 mole) peracetyl-β-D-maltopentaoside are dissolved in 200 ml anhydrous tetrahydrofuran 33 ml (0.3 mole) benzylamine are added thereto, while stirring, and stirring continued for 2 hours at ambient temperature with the exclusion of moisture. The reaction mixture is subsequently evaporated to dryness in a vacuum, the residue is dissolved in dichloromethane and the dichloromethane successively washed with, in each case, 400 ml 5 mole/liter hydrochloric acid, water, saturated aqueous sodium hydrogen carbonate solution and water. The organic phase is then dried over anhydrous sodium sulphate and heated to the boil under reflux with active charcoal. After filtering off the active charcoal, the filtrate is evaporated to dryness in a vacuum. The product can readily be used in the next step without purification. Yield: 140 g (97% of theory). TLC: silica gel 60 F$_{254}$ (Merck); toluene/acetone 7:5 v/v R$_f$=0.42

$^1$H-NMR (DMSO-d$_6$): 1.8–2.2 (s, 48H, CH$_3$CO) 3.8–5.5 (m, 35 H, H-1 - H-6) 5.7 (s, 1H, OH).

Literature: Helferich. B. and Portz, W., Chem. Ber., 86, 604/1953.

The following maltooligosaccharides were synthesized in a manner analogous to this procedure:

| sugar | yield | Rf (silica gel 60, toluene:acetone 7:4 v/v) |
|---|---|---|
| maltose | 96% | 0.45 |
| maltotriose | 96% | 0.40 |

EXAMPLE 3

Peracetylmaltopentaosyl-α-D-trichloroacetimidate 75 g (0.05 mole) hydroxy-α-D-peracetylmaltopentaoside and 25 ml (0.25 mole) trichloroacetonitrile are dissolved in 50 ml anhydrous dichloromethane. The solution is cooled to 0° C., 1.5 g (0.055 mole) sodium hydride are added portionwise thereto, while stirring, and the reaction mixture is then stirred for 2 hours at ambient temperature with the exclusion of moisture. Excess sodium hydride is separated off over a glass frit, the filtrate is filtered over a silica gel column (60 Merck, about 200 ml., diameter 6 cm.) and rinsed with 2 liters ethyl acetate. The filtrate is boiled under reflux with active charcoal, the active charcoal is filtered off and the filtrate is evaporated to dryness in a vacuum. Yield: 72 g (87.5% of theory) of colorless, foamy product.

TLC: silica gel 60 F$_{254}$ (Merck); toluene/acetone (7:4 v/v) Rf=0.58.

$^1$H-NMR (DMSO-d$_6$): 1.8–2.2 (s, 48H, CH$_3$CO) 3.8–5.5 (m, 35H, H-1 - H-6) 6.3 (s, 1H, NH).

Literature: Schmidt, R. and Stumpp, M., Liebigs Ann. Chem., 1983, 1249–1256.

Peracetylmaltotriose trichloroacetimidate was prepared analogously to this procedure; yield 93% of theory; Rf=0.45.

EXAMPLE 4

Resorufinyl-β-D-maltopentaoside 72 g (0.044 mole) peracetylmaltopentaosyl-α-D-trichloroacetimidate and 4.4 g (0.02 mole) resorufin are suspended in 1 liter of anhydrous dimethylformamide. With BF$_3$.OEt catalysis, the reaction mixture is stirred for 8 hours at 60° C. with the exclusion of moisture. After cooling to ambient temperature, the reaction mixture is filtered over aluminum oxide (about 500 ml) and rinsed with 5 liters ethyl acetate. The filtrate is evaporated to dryness in a vacuum, the residue is dissolved in 100 ml anhydrous methanol and deacetylated with 2 g sodium methoxide for 3 hours at ambient temperature with the exclusion of moisture. The suspension is evaporated to dryness in a vacuum, the residue is taken up in 100 ml water, adjusted to pH 6 with 2 mole/liter hydrochloric acid and applied to a Diaion column (about 500 ml/diameter 8 cm). The column is first eluted with 4 liters of water and then with 3 liters of 20% isopropanol solution.

The eluate is concentrated to about 40 ml and chromatographed over an RP-18 flash column (diameter 4 cm, height 39 cm) with 15% isopropanol as elution agent in 50 ml portions. The fractions which contain the resorufin maltopentaoside are combined, concentrated in a vacuum to about 20 ml and chromatographed over an RP-18 MPLC column in 10 ml portions with 15% isopropanol. The fractions which contain the product are combined, evaporated in a vacuum and subsequently lyophilized.

Yield: 2.8 g (14% theory) of orange lyophilisate.

HPLC: RP-18 column, 1 ml/min 17% isopropanol, rt= 2.95 minutes, content of resorufin-G$_5$: 97%. $^1$H-NMR (DMSO-d$_6$): 3.0–6.0 (m, 51H, OH, H-1–H-6) 6.2–8.0 (m, 6H, ArH).

Literature: Schmidt, R. and Grundler, G., Synthesis, 1981, 885–887.

EXAMPLE 5

Preparation of resorufinyl-$\beta$-D-maltooligosaccharides by the Königs-Knorr method 1. Acetobromo-$\alpha$-D-maltooligosaccharide 25 mMole of the peracetylated carbohydrate are dissolved in 50 ml glacial acetic acid. 50 ml hydrobromic acid (30%) in glacial acetic are added dropwise thereto and the reaction mixture is stirred at ambient temperature with the exclusion of moisture. Subsequently, 300 ml dichloromethane are added thereto and poured into 1 liter of ice water. The organic phase is separated off and successively shaken out with water, saturated aqueous sodium hydrogen carbonate solution and water. The organic phase is dried over anhydrous sodium sulphate and then evaporated to dryness in a vacuum. The product can be used in the subsequent reaction without further purification.

| sugar | yield | Rf (silica gel 60/ toluene:acetone = 7:4 v/v) |
|---|---|---|
| maltose | 88% | 0.72 |
| maltotriose | 88% | 0.65 |
| maltotetraose | 93% | 0.61 |
| maltopentaose | 91% | 0.57 |
| maltohexaose | 93% | 0.53 |
| maltoheptaose | 95% | 0.50 |

Literature: Brauns, J.A.C.S., 51, 1830–1929.

2. Resorufinyl-$\beta$-D-maltooligosaccharides:

50 mMole resorufin and 25 mMole silver oxide are suspended in 800 ml anhydrous acetonitrile with a molecular sieve (3Å) and boiled under reflux with the exclusion of moisture. 62.5 nMole of the acetobromo-$\alpha$-D-peraceytlmaltooligosaccharides in 200 ml anhydrous acetonitrile are added thereto and the reaction mixture boiled under reflux for 6 hours. It is then further stirred for 18 hours at ambient temperature, 10g of active charcoal are added thereto and then briefly boiled under reflux. The mixture is filtered over 100 g aluminum oxide (activity stage III/N) and rinsed with 5 liters ethyl acetate. The filtrate is evaporated to dryness in a vacuum, the residue is dissolved in 1 liter of anhydrous ethanol and stirred for 18 hours at ambient temperature with 5 g sodium methoxide, with the exclusion of moisture. The suspension is evaporated to dryness in a vacuum, the residue is dissolved in 200 ml water, adjusted to pH 7 and applied to a column filled with 500 ml Diaion-HP-20. It is washed with 15 liters of water and eluted with 10 liters of a 15% isopropanol solution. The eluate is evaporated in a vacuum to 100 ml and, corresponding to the imidate method, chromatographed on a MPLC column (RP-18) with isopropanol solution and lyophilized.

| sugar | yield | HPLC rt/% isopropanol | Rf (silica gel) butanol/glacial acetic acid/water = 50:15:25 (v/v/v) |
|---|---|---|---|
| maltotriose[a] | 15% | 3.52 min/17% | 0.32 |
| maltotetraose | 16% | 3.27 min/17% | 0.29 |
| maltopentaose | 14% | 2.95 min/17% | — |
| maltoheptaose | 10% | 2.60 min/17% | — |
| maltose[b] | 15% | — | 0.39 |

[a] In the case of resorufinyl-$\beta$-D-maltotriose, elution of the Diaion column with 25% isopropanol and chromatography on an RP-18 column with 25% isopropanol.
[b] In the case of resorufinyl-$\beta$-D-maltoside, elution of the Diaion column with 40% isopropanol. The product is evaporated to dryness in a vacuum, then dissolved in dimethylformamide and precipitated out with water. The precipitate is filtered off with suction and dried in a vacuum.

$^1$H-NMR (DMSO-d$_6$): maltose: 3.1–3.9 (m, 11H, OH, H-6) 4.4–5.7 (m, 10H, H-1 - H-5) 6.2–8.0 (m, 6H, ArH) maltotriose: 3.0–5.9 (m, 32H, OH, H-1 - H6) 6.2–8.0 (m, 6H, ArH).

EXAMPLE 6

Synthesis of protected resorufinyl-$\beta$-D- and p-nitrophenyl-$\alpha$-D-maltooligosaccharides 1 mMole resorufinyl or p-nitrophenyl-maltoside and 4 mMole of orthoester or acetyl are dissolved in 10 ml anhydrous dimethylformamide with a molecular sieve (3Å, fresh, activated), with the exclusion of moisture. 1 mMole p-toluenesulphonic acid is added thereto, with stirring, whereafter stirring is continued for 4 hours at ambient temperature. Subsequently, 20 ml water are added thereto, the reaction mixture is stirred for 20 minutes and filtered over DEAE-Sephacel (CO$_2^{2-}$). It is washed with 20% isopropanol, the filtrate is concentrated in a vacuum to 20 ml and fractionally chromatographed over an RP-18 MPLC column with 18–60% isopropanol. The product fractions are combined, evaporated in a vacuum and lyophilized. In the case of resorufinyl-$\beta$-D-maltoside the protected compounds are precipitated from dimethylformamide/water. The compounds used and the physical date of the products are given in the following Table I.

EXAMPLE 7

Synthesis of end group-protected maltooligosaccharides according to the Mitsunobu reaction.

1 mMole resorufinyl-maltopentaoside are mixed in anhydrous dimethylformamide with 2 mMole of the carboxylic acid in question, triphenylphosphine and diethylazodicarboxylate and stirred for 16 hours at ambient temperature with the exclusion of moisture. 20 ml of water are then added thereto and the resultant precipittae is filtered off over a Seitz filter. The filtrate is concentrated in a vacuum to about 8 ml and chromatographed over an RP-18 MPLC column with 18% isopropanol. The product fractions are combined, evaporated in a vacuum and lyophilized. The products in question are identical with the products produced by the orthoester method (Example 6) and show the same physical data (see the following Table I).

TABLE I

| product | rt (HPLC, RP-18, 1 ml/min), ret. time/% iso-propanol | rf (TLC, silica gel/ butanol/glacial acetic acid/water, 50:15:25 v/v/v) | ¹H-NMR (DMSO-d₆) | ortho ester or acetal used (protective group) | % isopropanol in the case of chromato-graphy | yield |
|---|---|---|---|---|---|---|
| resorufinyl-β-D-maltopentaosyl formate | 3.19 min/17% | — | 3.2–5.6(m, 49H, CH₂, OH, H-1-H-6) 5.0(s, 1H, HCOO) 7.0–8.0(m, 6H, Ar—H) | trimethyl ortho-formate | 20% | 38% |
| resorufinyl-β-D-maltopentaosyl (N,N-dimethyl-amino) formate | 3.19 min/17% | — | 2.9(s, 6H, CH₃); 3.2–5.6(m, 49H, CH₂, OH, H-1-H-6) 6.5–7.4 (m, 6H, Ar—H) | trimethyl ortho-N,N-dimethylamine formate** | 20% | 15% |
| resorufinyl-β-D-maltotriosyl acetate | 3.50 min/20% | 0.4 | — | trimethyl ortho-acetate | 25% | 20% |
| resorufinyl-β-D-maltotetraosyl acetate | 3.40 min/17% | 0.36 | — | trimethyl ortho acetate | 17% | 35% |
| resorufinyl-β-D-maltopentaosyl acetate | 3.16 min/17% | — | — | trimethyl ortho-acetate | 15% | 40% |
| resorufinyl-β-D-maltoheptaosyl acetate | 3.04 min/17% | — | — | trimethyl ortho-acetate | 17% | 25% |
| resorufinyl-β-D-maltopentaosyl propionate | 3.85 min/17% | — | — | trimethyl ortho-propionate | 20% | 25% |
| resorufinyl-β-D-maltopentaosyl butyrate | 3.30 min/25% | — | — | trimethyl ortho-butyrate | 20% | 20% |
| resorufinyl-β-D-maltotetraosyl isobutyrate | 4.20 min/17% | — | — | trimethyl ortho-isobutyrate* | 29% | 30% |
| resorufinyl-β-D-maltopentaosyl isobutyrate | 3.40 min/25% 4.73 min/17% | — | — | triethyl ortho-isobutyrate* | 20% | 24% |
| resorufinyl-β-D-maltopentaosyl cyclopropyl-carboxylate | 3.14 min/20% | — | 0.9–1.0(m, 4H, CH₂); 1.6(d, 1H, CH); 3.2–5.6(m, 49H, CH₂, OH, H-1-H-6); 6.5–7.4 (m, 5H, Ar—H) | trimethyl ortho-cyclo-propyl-carboxylate* | 20% | 15% |
| resorufinyl-β-D-maltopentaosyl cyclohexyl-carboxylate | 3.05 min/25% | — | 1.6(s, 10H, CH₂); 2.0(d, 1H, CH); 3.2–5.6(m, 49H, CH₂, OH, H-1-H-6); 6.5–7.4(m, 6H, Ar—H | trimethyl ortho-cyclo-hexyl-carboxylate* | 30% | 30% |
| resorufinyl-β-D-maltopentaosyl valerate | 3.62 min/40% | — | 0.7–1.0(m, 3H, CH₃); 1.0–1.8(m, 4H, CH₂); 2.1–2.4 m, 2H, CH₂CO); 3.0–6.0(m, 49H, OH, H-1-H-6); 6.2–8.0 (m, 6H, Ar—H) | trimethyl ortho-valerate | 40% | 15% |
| resorufinyl-β-D-maltopentaosyl pivalate | — | — | 1.0–1.2(m, 9H, CH₃); 3.0–6.0(m, 49H, CH₂, OH, H-1-H-6); 6.2–8.0 (m, 6H, Ar—H) | trimethyl ortho-pivalate* | 25% | 10% |
| resorufinyl-β-D-maltopentaosyl benzoate | 2.70 min/40% | — | 2.8–5.4(m, 49H, H-1-H-6, OH); 6.2–8.0(m, 11H, Ar—H) | trimethyl ortho-benzoate* | 25% | 10% |
| p-nitrophenyl-α-D-malto-heptaosyl acetate | 4.16 min/13% | — | — | trimethyl ortho-acetate | 15% | 20% |
| p-nitrophenyl-α-D-malto-heptaosyl isobutyrate | 5.50 min/13% | — | — | trimethyl ortho-isobutyrate* | 15% | 15% |
| 4,6-ethylidene-resorufinyl-β-D-maltoside | — | 0.62 | — | acetaldehyde-dimethyl-acetal | was precipitated from DMF with water | 32% |
| 4,6-ethylidene- | 2.53 min/40% | — | — | acetaldehyde- | 20% | 30% |

TABLE I-continued

| product | rt (HPLC, RP-18, 1 ml/min), ret. time/% iso-propanol | rf (TLC, silica gel/ butanol/glacial acetic acid/water, 50:15:25 v/v/v) | $^1$H-NMR (DMSO-$d_6$) | ortho ester or acetal used (protective group) | % isopropanol in the case of chromato-graphy | yield |
|---|---|---|---|---|---|---|
| resorufinyl-β-D-maltopenta-oside | | | | dimethyl-acetal | | |
| resorufinyl-β-D-maltopentaosyl thiophenyl-2-carboxylate | 5.08 min/17% | — | 3.2–5.6(m, 49H, CH$_2$, OH, H-1-H-6); 7.0–8.0(m, 9H, Ar—H) | trimethyl ortho-thiophenyl-2-carboxyl-ate* | 20% | 24% |
| resorufinyl-β-D-maltopentaosyl-2-methoxy propionate | 6.73 min/17% | — | 0.9–1.0(d, 3H, CH$_3$); 3.2–5.6(m, 54H, CH$_2$, OH, CH, H-1-H-6, CH$_3$O); 7.0–8.0(m, 6H, Ar—H) | trimethyl ortho-2-methoxy-propionate | 20% | 15% |

**prepared according to Federal Republic of Germany Patent Specification No. 1122936
*prepared according to Houben-Weyl, Vol. VI/3, 300–305

EXAMPLE 8

α-amylase determination

Reagent (end concentration in the test)
1 mMole/liter substrate (cf. Table II)
100 mMole/liter HEPES buffer (pH 7.1)
50 mMole/liter sodium chloride
10 mMole/liter magnesium chloride
30 U/liter α-glucosidase
1 U/liter β-glucosidase 1 ml of reagent and 0.25 ml of a sample of pathological human serum are mixed together and the mixture is tempered to 25° C. After a pre-incubation time of 4 minutes (lag phase), the extinction and the extinction change per minute (ΔE/min) is determined. The results for substrates (1), (2) and (4) and (6) according to the present invention in comparison with substrates (3) and (5) are demonstrated by the following Table II:

TABLE II

| substrate | blank ΔE/min. | sample ΔE/min. |
|---|---|---|
| 1) resorufinyl-β-D-G$_5$-acetate | 0.0140 | 0.535 |
| 2) resorufinyl-β-D-G$_5$-isobutyrate | 0.0091 | 0.590 |
| 3) resorufinyl-β-D-G$_5$ | 0.0182 | 0.430 |
| 4) resorufinyl-β-D-G$_5$-propionate | 0.0111 | 0.408 |
| 5) 4,6-ethylidene-resorufinyl-β-D-G$_5$ | 0.0018 | 0.0156 |
| 6) resorufinyl-β-D-G$_5$-butyrate | 0.0038 | 0.191 |

G$_5$ = maltopentaose

The results show that the new substrates have smaller blank values and, in several cases, give better, i.e., higher, turnover rates. This means that the substrate can give a better color development over a particular time range.

It will be understood that the specification and examples are illustrative but not limitative of the present invention and that other embodiments within the spirit and scope of the invention will suggest themselves to those skilled in the art.

We claim:

1. Compound useful in determining alphaamylase and of the formula

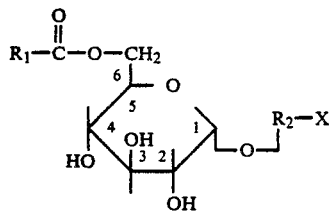

wherein R$_1$ is a hydrogen atom, straight chained or branched alkyl of from 1 to 4 carbons or 1-alkoxyalkyl radical, a cycloalkyl or hydrophilically substituted cycloalkyl radical of from 3 to 6 carbons, tetrahydropyranyl, an piperidinyl, N-methyl substituted piperidinyl or N-ethyl substituted piperidinyl, thiophenyl or 1,1-dioxo-tetrahydrothiopyranyl radical, an amino group or an amino group substituted at least once by methyl, ethyl, propyl or isopropyl, R$_2$ is an oligoglucoside residue with 2,3 or 4 glucose units and X is a hydrogen atom or an optically determinable residue.

2. Compound of claim 1, wherein R$_1$ is methyl, isopropyl, cyclopropyl or hydrophilically substituted cyclopropyl.

3. Compound of claim 1, wherein R$_2$ is an oligoglucoside residue of four units.

4. Compound of claim 1, wherein X is nitrophenyl, substituted nitrophenyl, resorufin, or substituted resorufin.

5. Compound of claim 1, designated:
resorufinyl-β-D-maltopentaosyl acetate;
resorufinyl-β-D-maltoheptaosyl acetate;
resorufinyl-β-D-maltopentaosyl propionate;
resorufinyl-β-D-maltopentaosyl butyrate;
resorufinyl-β-D-maltotetraosyl isobutyrate;
resorufinyl-β-D-maltopentaosyl formate;
resorufinyl-β-D-maltopentaosyl (N,N-dimethylamino) formate;
resorufinyl-β-D-maltotriosyl acetate;
resorufinyl-β-D-maltotetraosyl acetate;
resorufinyl-β-D-maltopentaosyl isobutyrate;
resorufinyl-β-D-maltopentaosyl cyclopropyl carboxylate;
resorufinyl-β-D-maltopentaosyl cyclohexyl carboxylate;
resorufinyl-β-D-maltopentaosyl valerate;
resorufinyl-β-D-maltopentaosyl pivalate;

resorufinyl-β-D-maltopentaosyl benzoate;

p-nitrophenyl-α-D-maltoheptaosyl acetate;

p-nitrophenyl-α-D-maltoheptaosyl isobutyrate;

resorufinyl-β-D-maltopentaosyl thiphenyl-2-carboxylate;

resorufinyl-β-D-maltopentaosyl 2-methoxy propionate; or resorufinyl-β-D-maltopentaoside.

6. Method for determining alpha amylase in a sample comprising contacting said sample to a compound of claim 1 in the presence of at least one of alpha glucosidase or beta glucosidase and determining X as an indication of alpha amylase in said sample.

7. Method of claim 6, comprising contacting said sample to a compound in the presence of alpha glucosidase.

8. Method of claim 6, comprising contacting said sample to a compound in the presence of beta glucosidase.

9. Method of claim 6, further comprising adding glucoanylase to said sample.

10. Reagent useful for the determination of alpha amylase in a sample, comprising:

0.5-2 mmole/liter of a compound of the formula

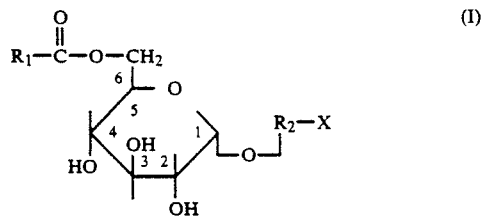

wherein $R_1$ is a hydrogen atom, straight chained alkyl of from 1 to 4 carbons or 1-alkoxyalkyl radical, a cycloalkyl or hydrophilically substituted cycloalkyl, radical of from 3 to 6 carbons, tetrahydropyranyl, piperidinyl, N-methyl substituted piperidinyl or N-ethyl substituted piperidinyl, thiophenyl or 1,1-dioxo-tetrahydrothiopyranyl radical an amino group or an amino group substituted at least once by methyl, ethyl, propyl or isopropyl, $R_2$ is an oligoglucoside residue with 2,3 or 4 glucose units and X is a hydrogen atom or an optically determinable residue, 30-100 mmole/liter Nacl;

at least one of 20-50 U/liter alpha glucosidase and 0.5-2 U/liter beta glucosidase, and 20-200 mmole/liter of a buffer at a pH of 6-8.

11. Reagent of claim 10, further comprising 5-20 U/ml glucoanylase.

12. Reagent of claim 10, further comprising 5-20 mmole/liter magnesium chloride.

* * * * *